(12) United States Patent
Salomon et al.

(10) Patent No.: US 11,135,343 B2
(45) Date of Patent: Oct. 5, 2021

(54) BLOOD COMPONENT POOLING DEVICE, SYSTEM AND METHOD

(71) Applicant: Fenwal, Inc., Lake Zurich, IL (US)

(72) Inventors: Alexandra Salomon, Evanston, IL (US); Julie Griep, St. Paul, MN (US); Kyungyoon Min, Kildeer, IL (US); Christopher J. Wegener, Libertyville, IL (US); Anand Raju, Addison, IL (US)

(73) Assignee: Fenwal, Inc., Lake Zurich, IL (US)

( * ) Notice: Subject to any disclaimer, the term of this patent is extended or adjusted under 35 U.S.C. 154(b) by 516 days.

(21) Appl. No.: 15/827,828

(22) Filed: Nov. 30, 2017

(65) Prior Publication Data

US 2018/0154054 A1    Jun. 7, 2018

Related U.S. Application Data

(60) Provisional application No. 62/428,833, filed on Dec. 1, 2016.

(51) Int. Cl.
*A61M 1/02* (2006.01)
*A61J 1/05* (2006.01)
*A61M 1/36* (2006.01)

(52) U.S. Cl.
CPC .......... *A61M 1/029* (2013.01); *A61J 1/05* (2013.01); *A61M 1/0209* (2013.01); *A61M 1/0281* (2013.01); *A61M 1/3692* (2014.02); *A61M 2202/0427* (2013.01); *A61M 2205/3393* (2013.01); *A61M 2209/082* (2013.01); *A61M 2209/084* (2013.01)

(58) Field of Classification Search
CPC .. A61M 1/029; A61M 1/0209; A61M 1/0281; A61M 1/3692; A61J 1/05
See application file for complete search history.

(56) References Cited

U.S. PATENT DOCUMENTS 3,737,096 A * 6/1973 Jones ............... A61M 1/3692
                                                    494/9
4,056,224 A    11/1977 Lolachi
(Continued)

FOREIGN PATENT DOCUMENTS

WO    WO98/28057    7/1998

OTHER PUBLICATIONS

European Search Report and Opinion dated Apr. 18, 2018, for Application No. 17204644.3-115.

*Primary Examiner* — Catharine L Anderson
*Assistant Examiner* — Arjuna P Chatrathi
(74) *Attorney, Agent, or Firm* — Cook Alex Ltd.

(57) ABSTRACT

A device for pooling a blood component stored in source containers includes a pump or pumps configured to pump a fluid in a first direction and a second direction and receive a pump line having a first end connected to the source containers. A pool clamp is configured to receive a pool line having a first end connected to a second end of the pump line and a second end connected to a pool container. A wash clamp is configured to receive a wash line having a first end connected to the second end of the pump line and a second end connected to a wash media container. A controller is configured to open the pool clamp, close the wash clamp and operate the pump in the first direction and to alternatively close the pool clamp, open the wash clamp and operate the pump in the second direction.

13 Claims, 7 Drawing Sheets

(56) References Cited

U.S. PATENT DOCUMENTS

| | | | | |
|---|---|---|---|---|
| 4,807,676 | A * | 2/1989 | Cerny | A61M 1/029 |
| | | | | 141/83 |
| 4,897,185 | A * | 1/1990 | Schuyler | A61M 1/3472 |
| | | | | 210/132 |
| 4,900,322 | A * | 2/1990 | Adams | A61M 1/0209 |
| | | | | 604/248 |
| 5,055,198 | A * | 10/1991 | Shettigar | A61M 1/3604 |
| | | | | 210/650 |
| 5,364,526 | A * | 11/1994 | Matkovich | A61M 1/0209 |
| | | | | 149/105 |
| 6,106,727 | A * | 8/2000 | Krasnoff | A61M 1/0227 |
| | | | | 210/739 |
| 6,284,142 | B1 | 9/2001 | Muller | |
| 7,037,428 | B1 * | 5/2006 | Robinson | A61M 1/3693 |
| | | | | 210/360.1 |
| 8,992,443 | B2 * | 3/2015 | Gable | A61B 5/150992 |
| | | | | 600/584 |
| 2002/0179544 | A1 * | 12/2002 | Johnson | A61M 1/3403 |
| | | | | 210/806 |
| 2003/0104349 | A1 * | 6/2003 | Bischof | A01N 1/02 |
| | | | | 435/2 |
| 2006/0122552 | A1 * | 6/2006 | O'Mahony | A61M 1/342 |
| | | | | 604/6.11 |
| 2011/0003675 | A1 * | 1/2011 | Dolecek | A61M 1/3698 |
| | | | | 494/7 |
| 2014/0199680 | A1 * | 7/2014 | Min | A61M 1/0236 |
| | | | | 435/2 |

* cited by examiner

BLOOD COMPONENT POOLING DEVICE, SYSTEM AND METHOD

CLAIM OF PRIORITY

This application claims the benefit of U.S. Provisional Application No. 62/428,833, filed Dec. 1, 2016, the contents of which are hereby incorporated by reference.

FIELD OF THE INVENTION

The present disclosure relates generally to the processing and storage of whole blood components and, in particular, to a device, system and method for pooling a component of whole blood.

BACKGROUND

Whole blood collected from donors is often separated into components that are extremely valuable for medical therapies. The whole blood is typically centrifuged using the "hard spin method" and stored in a container where a cellular layer and a supernatant layer are formed with a transition zone or layer between them. The sediment layer includes a concentration of red blood cells, while the supernatant layer includes plasma. The transition layer or zone, which is known as the "buffy coat," contains white blood cells, a concentration of platelets, red blood cells and plasma.

Platelets are the primary blood clotting component commonly needed by trauma victims and cancer patients. Given that most of the platelets reside in the buffy coat, in some processing methods, the buffy coat is separated from the remaining layers. A number of source bags containing buffy coats are then combined or "pooled" into a single bag for further processing.

The primary prior art process for pooling buffy coats is a manual approach that is both time consuming and tiring. More specifically, four to five source bags containing buffy coats are connected together in a sterile train configuration, with a bag containing a wash media of plasma and/or plasma additive solution (PAS) at the top of the train and a pooling bag at the bottom of the train. The top bag (containing the wash media) is hung from a stand so that the bags are oriented vertically with the pooling bag at the bottom. Hemostats are positioned on the tubing running between each bag of the train.

The hemostats are manipulated so that half of the wash media from the top bag is rinsed through each bag one by one due to gravity. Each bag is manipulated by the user after it receives the wash media so to mix the wash media with the cells remaining in the bag. This is again repeated with the second half of the wash media. The buffy coats and wash media are all collected in the pooling bag. The time required to set up the train is typically around fifteen minutes, and another ten minutes or so is required to perform the pooling process. In addition to being tedious, the manipulation of the bags to mix the wash media with the remaining cells is strenuous. There is also repeated physical stress to users in that they have to reach high and bend low to complete the pooling process.

Prior attempts at automating the pooling process involve centrifuge-like devices that take up additional valuable space in blood centers.

SUMMARY

Figure 1:
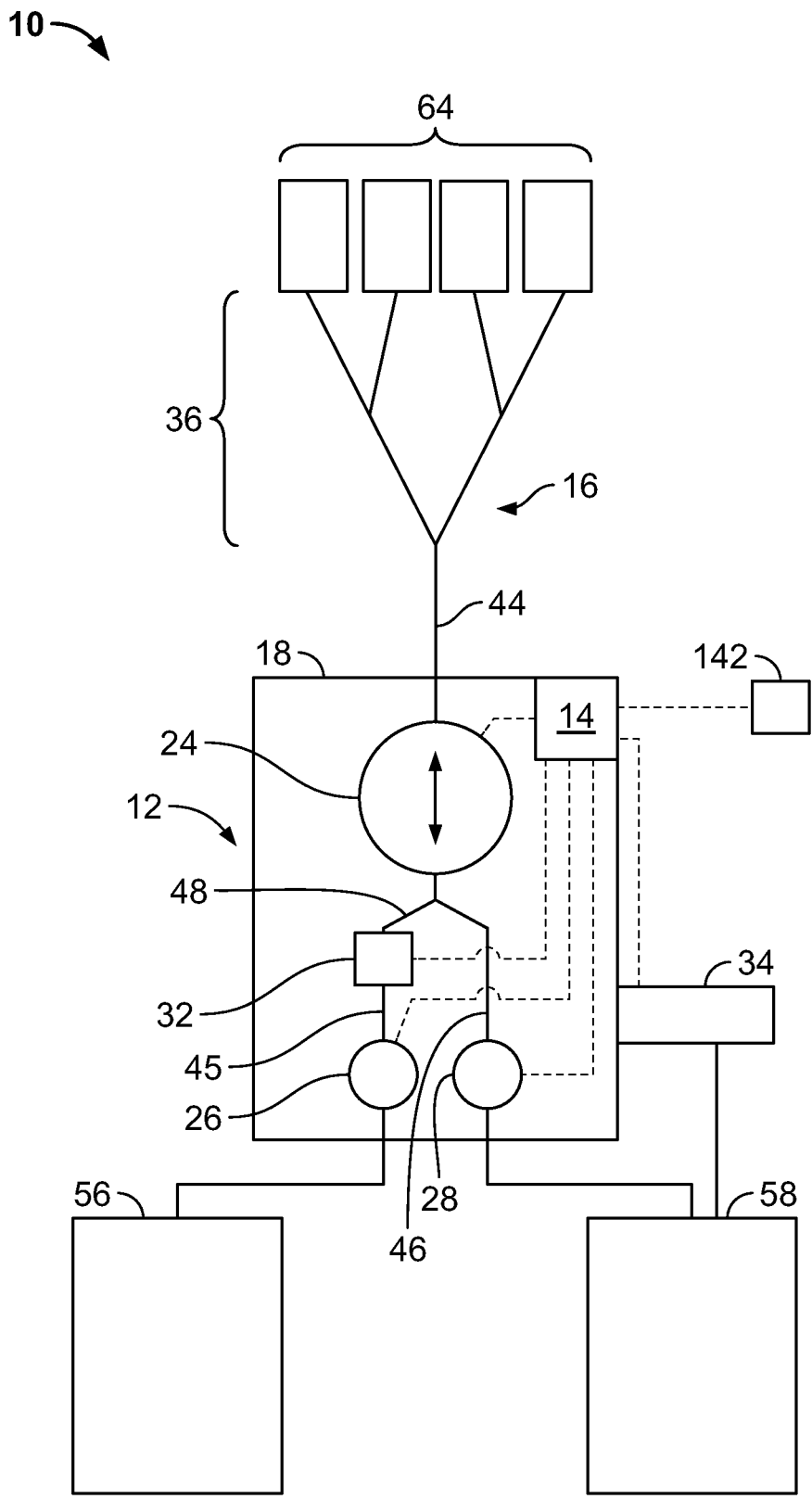
FIG. 1 is a schematic view of an embodiment of the blood component pooling system.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a device for pooling a blood component stored in a number of source containers includes a pump or pumps configured to pump a fluid in a first direction and a second direction. The pump or pumps are configured to receive a pump line having a first end connected to the plurality of source containers. A pool clamp is configured to receive a pool line having a first end connected to a second end of the pump line and a second end connected to a pool container. A wash clamp is configured to receive a wash line having a first end connected to the second end of the pump line and a second end connected to a wash media container. A controller is in communication with the pump or pumps, the pool clamp and the wash clamp. The controller is configured to open the pool clamp, close the wash clamp and operate the pump in the first direction and to alternatively close the pool clamp, open the wash clamp and operate the pump in the second direction.

In another aspect, a system for pooling a blood component stored in a number of source containers includes a disposable kit having a plurality of source lines configured to be connected to the source containers, a pump line having a first end connected to the source lines and a second end, a pool line having a first end connected to the second end of the pump line and a second end configured to be connected to a pool container and a wash line having a first end connected to the second end of the pump line and a second end configured to be connected to a wash media container. A pump or pumps are configured to pump a fluid in a first direction and a second direction. The pump or pumps receive the pump line. A pool clamp receives the pool line while a wash clamp receives the wash line. A controller is in communication with the pump or pumps, the pool clamp and the wash clamp. The controller is configured to (i) open the pool clamp, close the wash clamp and operate the pump in the first direction to transfer the blood component from the source containers to the pool container, (ii) close the pool clamp, open the wash clamp and operate the pump in the second direction to transfer the wash media to the source containers and (iii) open the pool clamp, close the wash clamp and operate the pump in the first direction to transfer contents of the source containers to the pool container.

In yet another aspect, a method for pooling a blood component stored in a number of source containers includes the steps of connecting the number of source containers to a number of source lines, connecting the number of source lines to a first end of a pump line, connecting a second end of the pump line to a first end of a pool line, connecting a second end of the pool line to a pool container, connecting the second end of the pump line to a first end of a wash line, connecting the second end of the wash line to a wash media container, closing the wash line and, while the pool line is open, pumping the blood component from the source containers to the pool container, closing the pool line and, while the wash line is open, pumping wash media to the source containers and opening the pool line, closing the wash line and pumping contents of the source containers to the pool container.

In still another aspect, a system for pooling a blood component stored in a plurality of source containers includes a disposable kit including a plurality of source lines configured to be connected to the plurality of source containers. A wash line is in fluid communication with the plurality of source lines and is configured to be connected to a wash media container. A pool line is in fluid communication with the plurality of source lines and is configured to be connected to a pool container. A pump is in fluid communication with the plurality of source lines and the wash line. A pool clamp receives the pool line. A controller is in communication with the pump and the pool clamp. The controller is configured to open the pool clamp to transfer the blood component from the plurality of source containers to the pool container, close the pool clamp and operate the pump to transfer the wash media to the plurality of source containers and open the pool clamp to transfer contents of the plurality of source containers to the pool container.

DETAILED DESCRIPTION OF EMBODIMENTS

While embodiments are described below in terms of buffy coats as the whole blood component, the invention may be used in the pooling of other blood components. In addition, while the containers for storing the blood component, wash media and pooled blood components are described below as being bags, other types of containers may be used.

Figure 2:
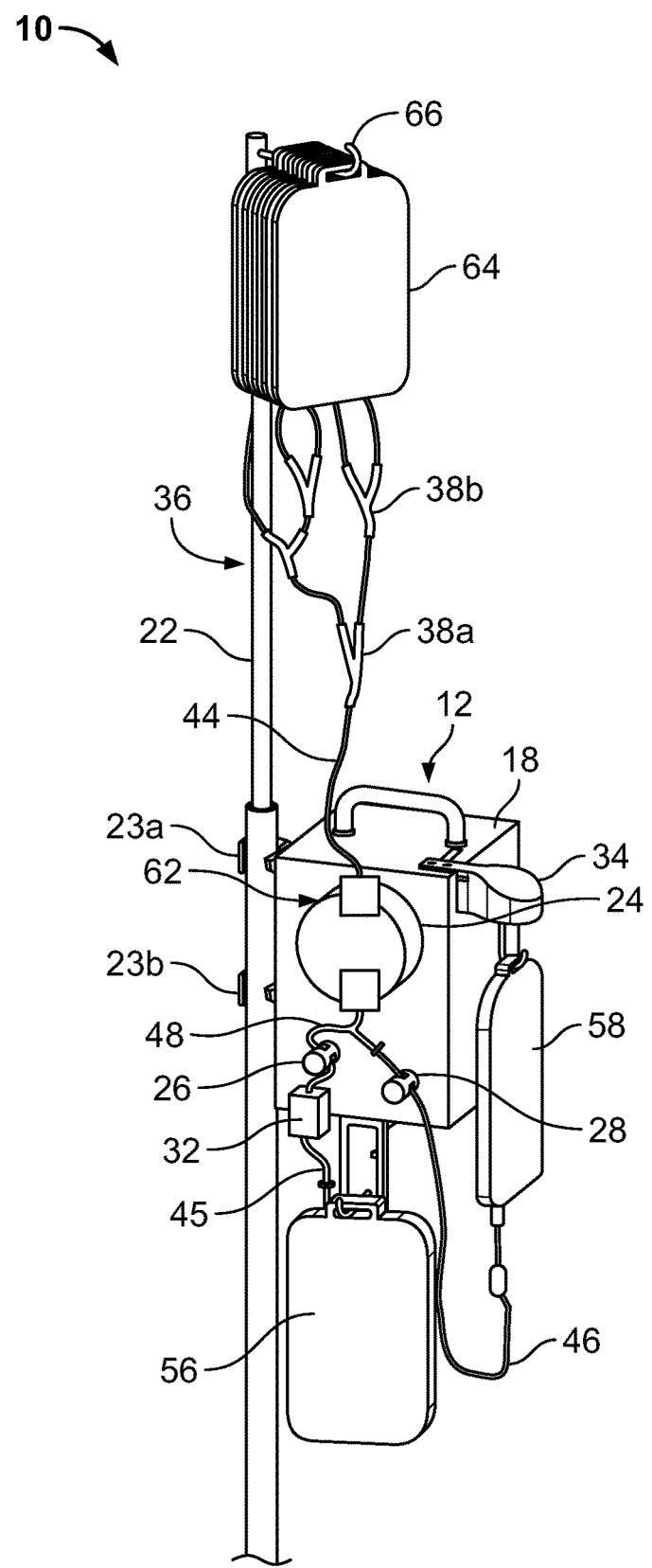
FIG. 2 is a perspective view of the system of FIG. 1.

An embodiment of a blood component pooling system is indicated in general at 10 in FIGS. 1 and 2. With reference to FIG. 1, the system has three main components: a physical electro-mechanical device, indicated in general at 12, the software that controls it via a controller 14, and a disposable kit, indicated in general at 16.

As illustrated in FIGS. 1 and 2, the blood component pooling device 12 includes a housing, indicated at 18, that may be mounted on a pole (22 in FIG. 2) via optional pole-mount clamps (23a and 23b in FIG. 2), set on a surface or otherwise positioned or mounted so as to be convenient for a user to operate. The housing contains a two-way tubing pump 24 and a pool tubing clamp 26 and a wash tubing clamp 28. As an example only, the pump may be a peristaltic pump of the type available from Fenwal, Inc. of Lake Zurich, Ill. The single, two-way pump 24 may of course be replaced by two one-way pumps. As examples only, the tubing clamps 26 and 28 may be solenoid pinch valves (as described below), motor-driven rotary pinch valves, linear actuators, stop cocks or any other type of automated clamping or valve device known in the art. In addition, the two separate clamps 26 and 28 can be replaced by a single, dual tube slot device where one tube slot may be opened while the other tube slot is closed so as to serve as both the pool clamp and the wash clamp.

The blood component pooling device also includes an optional air detector 32 and an optional weight scale 34.

While the clamps 26 and 28, air detector 32 and weight scale 34 are illustrated as attached to the housing 18 of the device, the components may otherwise be mounted or positioned in the vicinity of the device.

Figure 3:
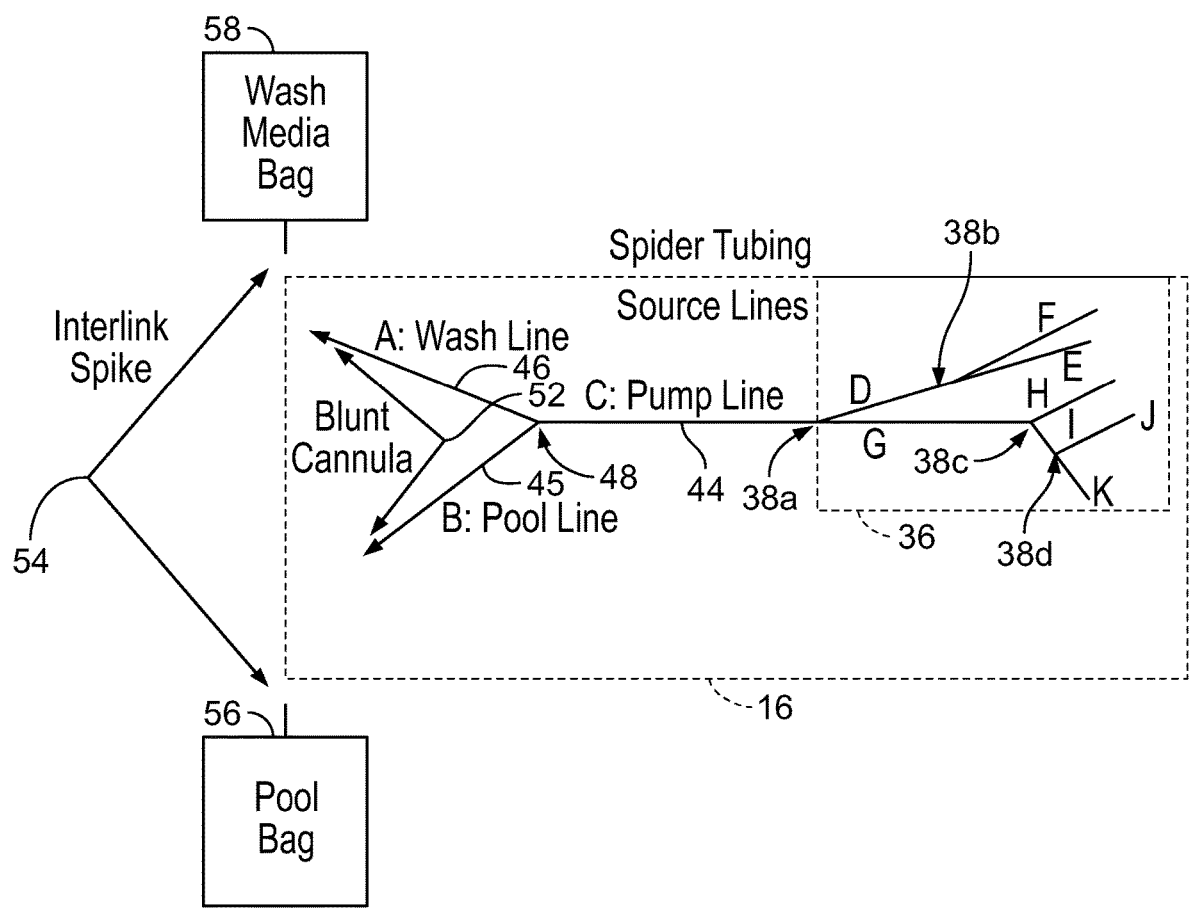
FIG. 3 is a schematic of the disposable kit of the system of FIGS. 1 and 2.

The disposable kit or spider is illustrated in FIG. 3 by surrounding phantom box 16. The kit includes source tubing lines, surrounded by phantom box 36 in FIG. 3, that are joined together by tubing Y-connectors 38a, 38b, 38c and 38d into one pump tubing line 44 that, as explained below, threads through the pump 24 (FIGS. 1 and 2). The number of source lines may be varied based upon the number of source bags being pooled. This line reduction can also occur via a manifold, T-connectors, or a custom made connector for the appropriate number of source bags.

The kit preferably minimizes the tubing as additional tubing results in additional losses of pooled cells and volume. As examples only, and with reference to the letter designations for the tubing lines of FIG. 3, the tubing lines may have lengths as follows: A=13½" (Wash Line), B=6" (Pool Line), C=7½"(Pump Line), D=12" (Source Line), E=6" (Source Line), F=6" (Source Line), G=9" (Source Line), H=9" (Source Line), I=2" (Source Line), J=8" (Source Line) and K=8" (Source Line).

The length of the source tubing lines 36 have also been chosen to make the flow from each side of a Y-connector equal to the ratio of bags on each side of the Y connector (i.e. J+K+I=2H since there are sources J and K versus source H) and to minimize differences in head height to allow the source bags to empty at about the same rate. This is not perfect though, as mathematically, this would require zero length when there are an odd number of bags. Additionally, line balancing does not account for differences in viscosity, which also impacts the flow, but these differences are assumed to be small. Regardless, the attempt at line balancing improves the performance of the system.

The pump tubing line 44 splits into pool tubing line 45 and wash tubing line 46 via a Y-connector 48. The ends 52 of tubing lines 45 and 46 are provided with blunt cannulas that are engaged by spikes 54 of the pool and wash bags 56 and 58 so that the bags are in fluid communication with the corresponding tube lines 45 and 46. Alternatively, the lines 45 and 46 may be sterile docked with the pool and wash bags 56 and 58, or any other arrangement for establishing a flow path may be used.

As illustrated in FIGS. 1 and 2, the pump tubing line 44 threads through two keepers or passages 62 (FIG. 2) of the pump 24 with the Y-connector 48 positioned after the pump. The pool tubing line 45 threads through the air detector 32 and then through pool clamp 26 before connecting to the pool bag 56, which may be hung on a hook or otherwise supported. Alternatively, the pool tubing line may first thread through the pool clamp 26 and then through the air detector 32 before connecting to the pool bag 56. The wash tubing line 46 connects to the wash media bag 58 hanging on the weight scale 34. In embodiments where the weight scale 34 is omitted, the wash media bag may be instead hung on a hook or otherwise supported. The source tubing lines 36 are connected to source bags 64 of whatever blood component is to be pooled. While four source bags 64 are illustrated, an alternative number of source bags may be provided and pooled. As illustrated in FIG. 2, these may be hung on a hook 66 positioned on the pole 22 above the device 12, although they could alternatively be placed on a surface or hanging from the device itself.

As an example only, the wash media bag may contain PAS and/or plasma.

Figure 4A:
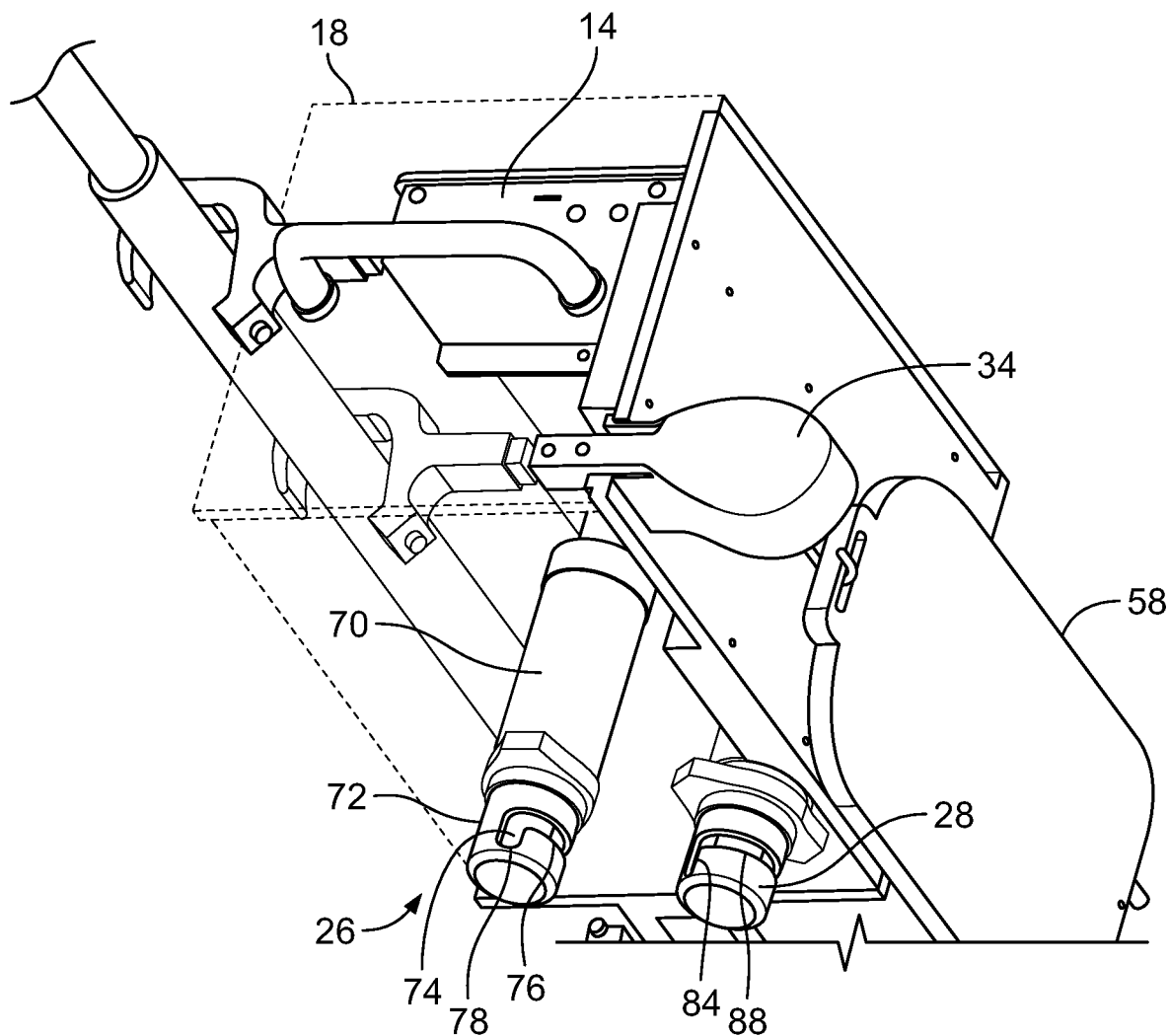
FIGS. 4A and 4B are top and bottom perspective views, respectively, of the blood component pooling device of the systems of FIGS. 1 and 2.
Figure 4B:
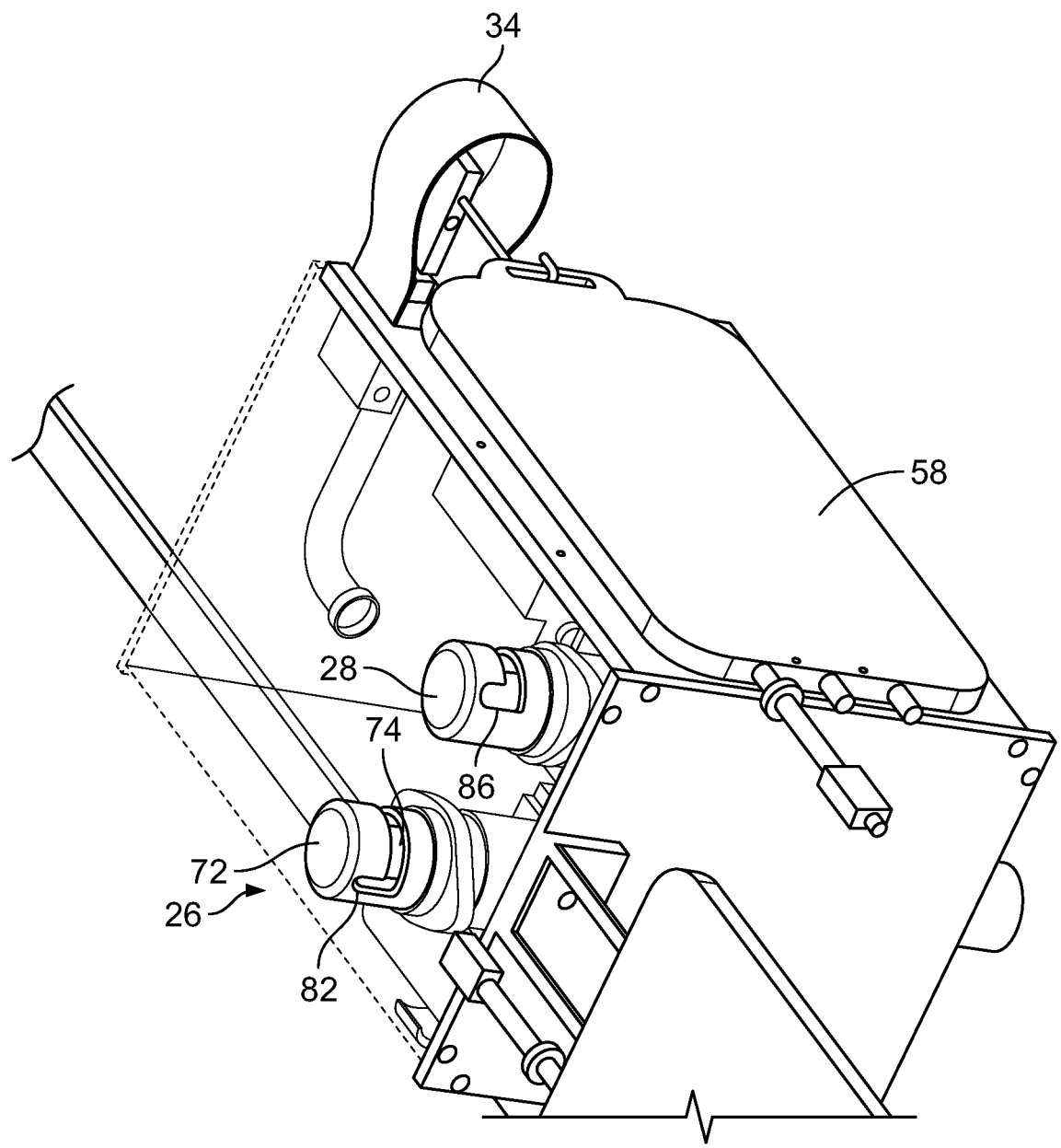

As illustrated in FIGS. 4A and 4B, pool clamp 26 features a body having a solenoid housing 70 and a head 72. The solenoid housing contains a solenoid mechanism that, when activated, extends a plunger 74 into the head 72 of the housing, as illustrated in FIGS. 4A and 4B. The head includes a slot 76 that includes a first notched portion, indicated at 78 in FIG. 4A, and a second notched portion, indicated at 82 in FIG. 4B. Notched portion 78 opposes notched portion 82. When the solenoid is not activated, and the plunger 74 is retracted into the solenoid housing 70, the pool tubing line may be inserted into the slot 76 of the head and placed so as to be retained within the notches 78 and 82. As a result, when the solenoid is activated, and the plunger extends into the head 72, the pool tubing line is pinched closed so that fluid does not flow through it. Wash clamp 28 features a similar construction so that the wash tubing line may be retained within the notches 84 and 86 of slot 88 and pinched closed when the solenoid of the clamp is activated.

As noted previously, alternative types of clamping devices, including a single clamping device, may be used.

With reference to FIG. 1, preparing the system 10 for use involves sterile docking the source tubing lines 36 into the source blood component bags 64, or otherwise introducing the source fluids to the kit path, and loading the remaining portions of the kit 16 through the device components (as described above) before opening the source bag welds.

As illustrated in FIG. 1, the device includes a controller 14 (also shown in FIG. 4A) which is in electrical communication with the pump 24, clamps 26 and 28, air detector 32 and weight scale 34. The controller is programmed to perform the processing of FIG. 5, which will now be described, along with operation of the device and system. In alternative embodiments, the controller may be commanded either externally or by buttons on the device to perform the processing of FIG. 5.

Figure 5:
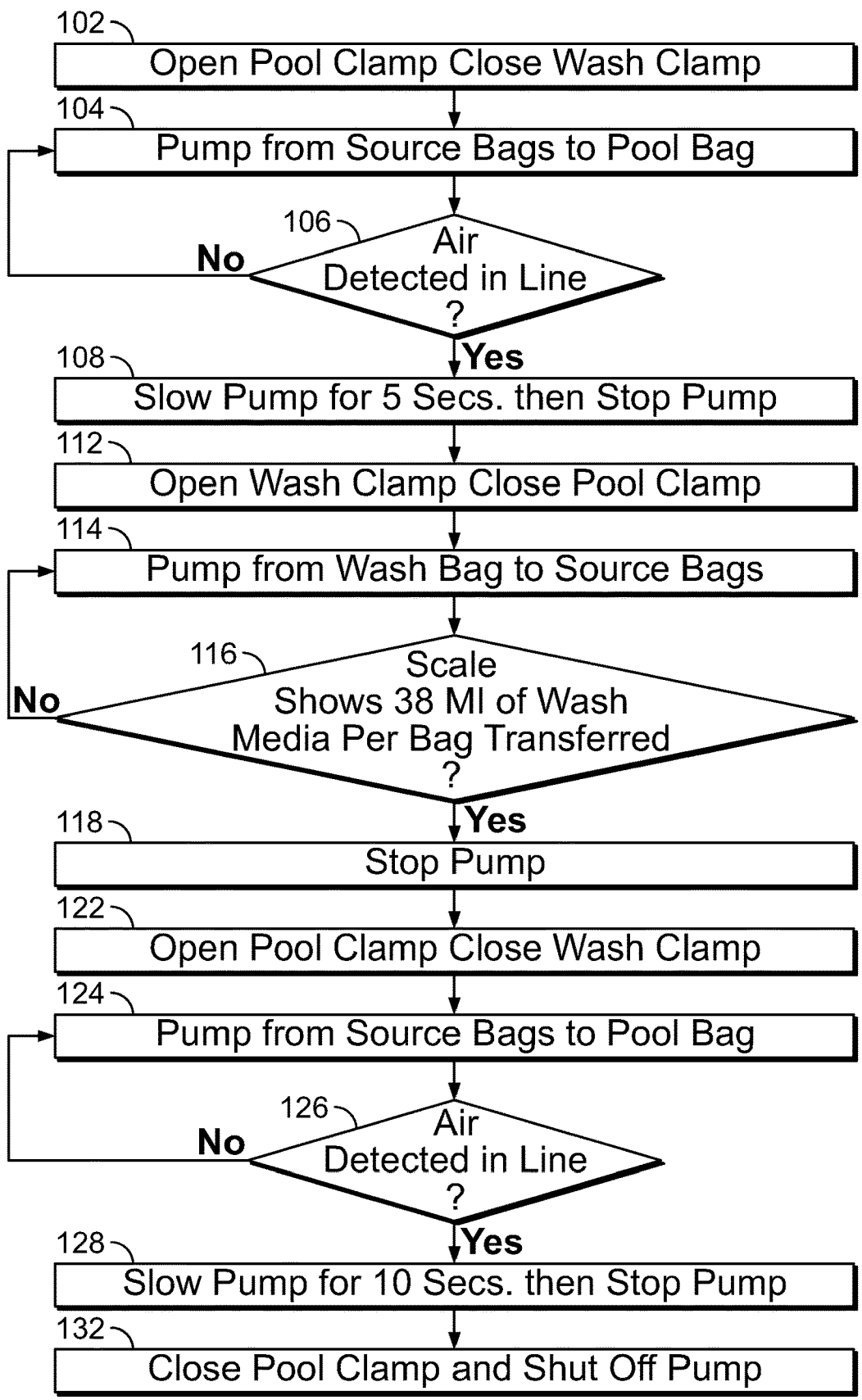
FIG. 5 is a flow chart illustrating the processing performed by the controller of the system of FIGS. 1, 2, 4A and 4B.

As indicated by block 102 of FIG. 5, the controller first opens the pool clamp and closes the wash clamp. As indicated by block 104, the controller next commands the pump to flow downward, draining the source blood component bags into the pool bag. As indicated by block 106, the air detector monitors the flow into the pool bag for the presence of air. As indicated by block 108, once air is detected, the pump slows and continues pumping for approximately five seconds or other time period (the timing can be adjusted).

Next, as indicated by block 112, the pool clamp closes, the wash clamp opens, and, as indicated by block 114, the pump reverses and starts flowing upwards so that the wash media from the wash media bag flows toward the source bags to rinse them and recover additional cells.

The wash media flows into the mostly empty blood component bags until, as indicated by block 116, the weight scale detects that approximately 38 mL of wash media per source bag has been transferred. In embodiments where the weight scale is omitted, the transfer may be instead be timed by the controller and terminated when the elapsed time corresponds to the proper amount of wash media transferred. This is to achieve a preferred fluid balance of the supernatant of, for example, 35% plasma to 65% additive solution, with the platelets (and small amounts of other cellular matter such as white and red blood cells) as the sediment layer or suspended within the supernatant in the pool bag. This ratio is an example only for when buffy coats are in the source bags and would need to be recalculated for other blood components. The ratio is desirable because this is the FDA approved ratio of plasma-to-additive ratio for platelets in the United States (and several other countries). Furthermore, supplementing plasma with additive solution is preferred because plasma can be sold on the market (as "source plasma") to pharma companies who use it as a raw material for drugs (such as IgG, coagulant factors, etc). The plasma is sold by the mL, so the less plasma that is required to supplement the buffy coat, the more can be sold, and the more economical the model for blood centers. In addition, reducing plasma reduces the risk of transfusion-related acute lung injury (TRALI) in transfusion recipients.

Once the appropriate amount of wash media has been pumped into the source bags, the pump stops (block 118) and the wash clamp closes while the pool clamp opens (block 122). As indicated by block 124, the pump starts flowing from the source blood component bags towards the pool bag again. Once air is detected (block 126), the pump slows and continues pumping for approximately ten seconds or other time period (block 128) to ensure that as many cells as possible make it into the pool bag (the timing can be adjusted). As indicated by block 132, the pool clamp then closes and the pump stops. This is the end of the pooling procedure and the user may proceed with post processing.

The controller 14 (FIG. 1) may optionally be programmed or otherwise configured to "burp" the pool bag after block 132 of FIG. 5. With reference to FIG. 1, this may be accomplished by opening the pool clamp 26 and running the pump 24 to pump fluid from the pool bag 56 towards the source bags 64. As a result, excess air is withdrawn from the pool bag 56. This operation continues until the air detector 32 detects liquid. The controller then reverses the direction of pump 24, and pumping occurs at a slow speed for approximately 3 seconds (an alternative time may be used) so that any liquid in the pool line 45 is returned to the pool bag 56.

The above procedure is very time efficient in that the user only needs to open the welds of the source product bags and then select "Go" on the controller to initiate the pooling process. The automated process may then be completed, as an example only, in less than 3.5 minutes.

As indicated previously, the air detector and weight scale (32 and 34 of FIG. 1, respectively) are optional components. In an embodiment that omits either component, or both components, the operation of the pump may be based on predetermined times based on pump flow rates and/or source blood component and wash media bag volumes.

Each source blood component bag (64 in FIGS. 1 and 2) may optionally be provided with bar coding indicating what blood component is present in the bag. A bar coding reader (indicated at 142 in FIG. 1) may then optionally be provided for the device, with the bar coding reader in communication with the device controller 14. In such an embodiment, the controller programming adjusts the slow pumping times (blocks 108 and 128 of FIG. 5) and the scale weight amount (block 116 of FIG. 5) based on the blood component being pooled. Other functionality of the controller may be altered based on the blood component indicated as present in the source bags. The type of blood component present in the source bags may alternatively be communicated to the controller via a device display, which may or may not include a menu with options, or buttons/knobs, a USB port or any other input component or arrangement.

Figure 6:
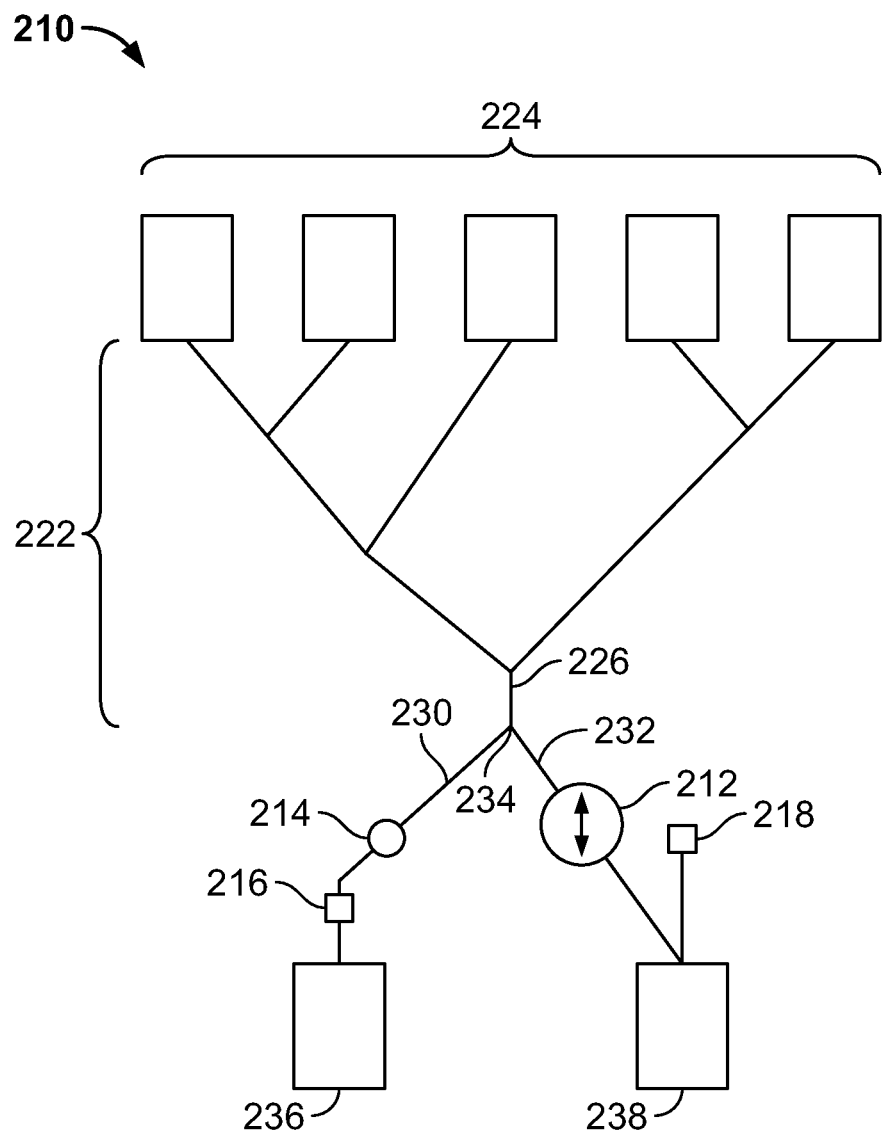
FIG. 6 is a schematic view of an alternative embodiment of the blood component pooling system.

In an alternative embodiment of a blood component pooling system, indicated in general at 210 in FIG. 6, a single-direction or one-way tubing pump 212 and a pool tubing clamp 214 are provided. The pump 212 and pool tubing clamp 214 may be part of a single device or two separate devices.

As in the embodiment described above, an optional air detector 216 and an optional weight scale 218 are also provided.

As in the embodiment described above, a disposable kit 222, featuring a number of Y-connectors, connects a number of source bags 224 into a single tubing line 226. While six source bags are illustrated at 224, and alternative number of source bags may be accommodated for pooling. The line reduction can also occur via a manifold, T-connectors, or a custom made connector for the appropriate number of source bags.

The single tubing line 226 splits into pool tubing line 230 and wash tubing line 232 via a Y-connector 234, and are in fluid communication with pool and wash bags 236 and 238, respectively.

As illustrated in FIG. 6, the wash tubing line 232 threads through the pump 212 and then connects to the wash bag 238, while the pool tubing line 230 threads through the pool tubing clamp 214 and the air detector 216 and then connects to the pool bag 236. Alternatively, the pool tubing line may first thread through the air detector 216 and then pool tubing clamp 214 before connecting to the pool bag.

As an example only, the wash media bag 238 may contain PAS and/or plasma.

As in the embodiment described previously, the system 210 includes a controller which is in electrical communication with the pump 212, clamp 214, air detector 216 and weight scale 218. The controller is programmed to perform the processing as follows. In alternative embodiments, the controller may be commanded either externally or by buttons on the device to perform the following processing.

The controller first opens the pool clamp 214 and the source blood component bags 224 drain into the pool bag 236 by gravity. The air detector 216 monitors the flow into the pool bag for the presence of air. Once air is detected, the pool tubing clamp remains open for approximately five seconds or other time period (the timing can be adjusted).

Next, the pool clamp closes, and the pump 212 is activated so that the wash media from the wash media bag 238 flows toward the source bags 224 to rinse them and recover additional cells.

The wash media flows into the mostly empty blood component bags until the weight scale 218 detects that approximately 38 mL of wash media per source bag has been transferred. In embodiments where the weight scale is omitted, the transfer may be instead be timed by the controller and terminated when the elapsed time corresponds to the proper amount of wash media transferred. As in the embodiment presented previously, this ratio is an example only for when buffy coats are in the source bags and would need to be recalculated for other blood components.

Once the appropriate amount of wash media has been pumped into the source bags 224, the pump 212 stops and the pool tubing clamp opens. As a result, fluid starts flowing from the source blood component bags 224 towards the pool bag 236 again. Once air is detected (by air detector 216), the pool tubing clamp 214 remains open for approximately ten seconds or other time period to ensure that as many cells as possible make it into the pool bag 236 (the timing can be adjusted). The pool tubing claim 214 then closes. This is the end of the pooling procedure and the user may proceed with post processing.

The embodiments described above solve the technical problems created by the time consuming and physically demanding manual prior art processes because the users don't have to manually manipulate the blood components to pool them. It also creates a more consistent platelet product, for example recovering >95% of platelets introduced into the system via the source blood component bags.

ASPECTS

Aspect 1. A device for pooling a blood component stored in a plurality of source containers including a pump or pumps configured to pump a fluid in a first direction and a second direction, said pump or pumps configured to receive a pump line having a first end connected to the plurality of source containers; a pool clamp configured to receive a pool line having a first end connected to a second end of the pump line and a second end connected to a pool container; a wash clamp configured to receive a wash line having a first end connected to the second end of the pump line and a second end connected to a wash media container; a controller in communication with the pump or pumps, the pool clamp and the wash clamp, said controller configured to open the pool clamp, close the wash clamp and operate the pump in the first direction and to alternatively close the pool clamp, open the wash clamp and operate the pump in the second direction.

Aspect 2. The device of aspect 1 wherein the pump or pumps are configured to removably receive the pump line, the pool clamp is configured to removably receive the pool line and the wash clamp is configured to removably receive the wash line.

Aspect 3. The device of any one of aspects 1 and 2 wherein the pool clamp and the wash clamp are solenoid pinch clamps.

Aspect 4. The device of any one of aspects 1-3 further comprising an air detector configured to receive the pool line and in communication with the controller, said controller configured to slow a speed of the pump in the first direction for a preset time when air in the pool line is detected by the air detector.

Aspect 5. The device of any one of aspects 1-4 further comprising a weight scale configured to support the wash media container and in communication with the controller, said controller configured to terminate operation of the pump in the second direction when the weight scale detects a preset weight of the wash media container.

Aspect 6. The device of any one of aspects 1-5 further comprising a housing to which the pump or pumps, pool clamp and wash clamp are mounted, said housing being configured to mount on a support pole.

Aspect 7. A system for pooling a blood component stored in a plurality of source containers includes a disposable kit including: i) a plurality of source lines configured to be connected to the plurality of source containers; ii) a pump line having a first end connected to the plurality of source lines and a second end; iii) a pool line having a first end connected to the second end of the pump line and a second end configured to be connected to a pool container; iv) a wash line having a first end connected to the second end of the pump line and a second end configured to be connected to a wash media container; a pump or pumps configured to pump a fluid in a first direction and a second direction, said pump or pumps receiving the pump line; a pool clamp receiving the pool line; a wash clamp receiving the wash line; a controller in communication with the pump or pumps, the pool clamp and the wash clamp, said controller configured to: i) open the pool clamp, close the wash clamp and operate the pump in the first direction to transfer the blood component from the plurality of source containers to the pool container; ii) close the pool clamp, open the wash clamp and operate the pump in the second direction to transfer the wash media to the plurality of source containers; and iii) open the pool clamp, close the wash clamp and operate the pump in the first direction to transfer contents of the plurality of source containers to the pool container.

Aspect 8. The system of Aspect 7 wherein the pump or pumps are configured to removably receive the pump line, the pool clamp is configured to removably receive the pool line and the wash clamp is configured to removably receive the wash line.

Aspect 9. The system of any one of Aspects 7 and 8 wherein the pool clamp and the wash clamp are solenoid pinch clamps.

Aspect 10. The system of any one of Aspects 7-9 further comprising an air detector receiving the pool line and in communication with the controller, said controller configured to slow a speed of the pump in the first direction for a preset time when air in the pool line is detected by the air detector.

Aspect 11. The system of Aspect 10 wherein the controller is also configured to open the pool clamp and operate the pump in the second direction until liquid is detected by the air detector and then operate the pump in the first direction for a preset time.

Aspect 12. The system of any one of Aspects 7-11 further comprising a weight scale configured to support the wash media container and in communication with the controller, said controller configured to terminate operation of the pump in the second direction when the weight scale detects a preset weight of the wash media container.

Aspect 13. A method for pooling a blood component stored in a plurality of source containers includes the steps of: connecting the plurality of source containers to a plurality of source lines; connecting the plurality of source lines to a first end of a pump line; connecting a second end of the pump line to a first end of a pool line; connecting a second end of the pool line to a pool container; connecting the second end of the pump line to a first end of a wash line; connecting the second end of the wash line to a wash media container; closing the wash line and, while the pool line is open, pumping the blood component from the plurality of source containers to the pool container; closing the pool line and, while the wash line is open, pumping wash media to the plurality of source containers; opening the pool line, closing the wash line and pumping contents of the plurality of source containers to the pool container.

Aspect 14. The method of Aspect 13 wherein the steps of closing the wash line and, while the pool line is open, pumping the blood component from the plurality of source containers to the pool container; closing the pool line and, while the wash line is open, pumping wash media to the plurality of source containers include clamping the wash line closed and the step of closing the pool line and, while the wash line is open, pumping wash media to the plurality of source containers includes clamping the pool line closed.

Aspect 15. The method of any one of claims 13 and 14 further comprising the steps of monitoring the pool line for air during the steps of closing the wash line and, while the pool line is open, pumping the blood component from the plurality of source containers to the pool container; and opening the pool line, closing the wash line and pumping contents of the plurality of source containers to the pool container, and slowing the pumping for a predetermined time period when air is detected in the pool line.

Aspect 16. The method of any one of Aspects 13-15 further comprising the step of weighing the wash media container during step of closing the pool line and, while the wash line is open, pumping wash media to the plurality of source containers and terminating pumping when a weight of the wash media container drops to a predetermined weight.

Aspect 17. The method of any one of Aspects 13-16 further comprising the steps of: opening the pool clamp and pumping air from the pool container to the source containers until liquid is detected; and pumping the detected liquid to the pool container.

Aspect 18. A system for pooling a blood component stored in a plurality of source containers comprising: a disposable kit including a plurality of source lines configured to be connected to the plurality of source containers; a wash line in fluid communication with the plurality of source lines and configured to be connected to a wash media container; a pool line in fluid communication with the plurality of source lines and configured to be connected to a pool container; a pump in fluid communication with the plurality of source lines and the wash line; a pool clamp receiving the pool line; a controller in communication with the pump and the pool clamp, said controller configured to: i) open the pool clamp to transfer the blood component from the plurality of source containers to the pool container; ii) close the pool clamp and operate the pump to transfer the wash media to the plurality of source containers; and iii) open the pool clamp to transfer contents of the plurality of source containers to the pool container.

Aspect 19. The system of Aspect 18 wherein the pool line is configured to transfer the blood component and contents of the plurality of source containers to the pool container by gravity.

Aspect 20. The system of Aspect 18 wherein the pump is a single-direction pump.

Aspect 21. The system of any one of Aspects 18-20 further comprising an air detector receiving the pool line and in communication with the controller, said controller configured to close the pool clamp after a period of time when air in the pool line is detected by the air detector.

Aspect 22. The system of any one of Aspects 18-21 further comprising a weight scale configured to support the wash media container and in communication with the controller, said controller configured to terminate operation of the pump when the weight scale detects a preset weight of the wash media container.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A device for pooling a blood component stored in a plurality of source containers comprising:
   a. a pump or pumps configured to pump a fluid in a first direction and a second direction, said pump or pumps configured to removably receive a pump line having a first end connected to the plurality of source containers;
   b. a pool clamp configured to removably receive a pool line having a first end connected to, and in continuous fluid communication with, a second end of the pump line and a second end connected to a pool container;
   c. a wash clamp configured to removably receive a wash line having a first end connected to, and in continuous fluid communication with, the second end of the pump line and a second end connected to a wash media container;
   d. a controller in communication with the pump or pumps, the pool clamp and the wash clamp, said controller configured to open the pool clamp, close the wash clamp and then operate the pump in the first direction and to alternatively close the pool clamp, open the wash clamp and then operate the pump in the second direction.

2. The device of claim 1 wherein the pool clamp and the wash clamp are solenoid pinch clamps.

3. The device of claim 1 further comprising an air detector configured to receive the pool line and in communication with the controller, said controller configured to slow a speed of the pump in the first direction for a preset time and then stop the pump after the preset time when air in the pool line is detected by the air detector.

4. The device of claim 3 wherein the controller is configured to close the pool clamp, open the wash clamp and initiate operation of the pump in the second direction after the pump is stopped after the preset time.

5. The device of claim 1 further comprising a weight scale configured to support the wash media container and in communication with the controller, said controller configured to terminate operation of the pump in the second direction when the weight scale detects a preset weight of the wash media container and then close the wash clamp, open the pool clamp and initiate operation of the pump in the first direction.

6. The device of claim 1 further comprising a housing to which the pump or pumps, pool clamp and wash clamp are mounted, said housing being configured to mount on a support pole.

7. A system for pooling a blood component stored in a plurality of source containers comprising:
   a. a disposable kit including:
      i) a plurality of source lines configured to be connected to the plurality of source containers;
      ii) a pump line having a first end connected to the plurality of source lines and a second end;
      iii) a pool line having a first end connected to, and in continuous fluid communication with, the second end of the pump line and a second end configured to be connected to a pool container;
      iv) a wash line having a first end connected to, and in continuous fluid communication with, the second end of the pump line and a second end configured to be connected to a wash media container;
   b. a pump or pumps configured to pump a fluid in a first direction and a second direction, said pump or pumps removably receiving the pump line;
   c. a pool clamp removably receiving the pool line;
   d. a wash clamp removably receiving the wash line;
   e. a controller in communication with the pump or pumps, the pool clamp and the wash clamp, said controller configured to:
      i) open the pool clamp, close the wash clamp and then operate the pump in the first direction to transfer the blood component from the plurality of source containers to the pool container;
      ii) close the pool clamp, open the wash clamp and then operate the pump in the second direction to transfer the wash media to the plurality of source containers; and
      iii) open the pool clamp, close the wash clamp and then operate the pump in the first direction to transfer contents of the plurality of source containers to the pool container.

8. The system of claim 7 wherein the pump or pumps include a single two-way pump and wherein the second end of the pump line includes a Y-connector to which the first ends of the pool and wash lines are connected.

9. The system of claim 7 wherein the pool clamp and the wash clamp are solenoid pinch clamps.

10. The system of claim 7 further comprising an air detector receiving the pool line and in communication with the controller, said controller configured to slow a speed of the pump in the first direction for a preset time when air in the pool line is detected by the air detector.

11. The system of claim 10 wherein the controller is also configured to open the pool clamp and operate the pump in the second direction until liquid is detected by the air detector and then operate the pump in the first direction for a preset time.

12. The system of claim 7 further comprising a weight scale configured to support the wash media container and in communication with the controller, said controller configured to terminate operation of the pump in the second direction when the weight scale detects a preset weight of the wash media container.

13. The system of claim 7 wherein the pump or pumps includes a single-direction pump.

* * * * *